United States Patent [19]

Mahoney et al.

[11] Patent Number: 5,007,265
[45] Date of Patent: Apr. 16, 1991

[54] OPTICAL MONITOR FOR SUPERPLASTIC FORMING

[75] Inventors: Murray W. Mahoney, Camarillo, Calif.; Amit K. Ghosh, Ann Arbor, Mich.

[73] Assignee: Rockwell International, El Segundo, Calif.

[21] Appl. No.: 285,987

[22] Filed: Dec. 19, 1988

[51] Int. Cl.$^5$ .............................................. B21D 26/02
[52] U.S. Cl. ............................................ 72/37; 72/60; 72/709
[58] Field of Search ................... 29/421.1; 72/10, 32, 72/37, 38, 60, 709; 73/800; 228/105

[56] References Cited

U.S. PATENT DOCUMENTS

| | | | |
|---|---|---|---|
| 4,181,000 | 1/1980 | Hamilton et al. | 72/60 |
| 4,233,829 | 11/1980 | Hamilton et al. | 72/60 X |
| 4,233,831 | 11/1980 | Hamilton et al. | 72/60 |
| 4,489,579 | 12/1984 | Daime et al. | 72/38 |
| 4,667,095 | 5/1987 | Hatanaka et al. | 73/800 X |
| 4,811,582 | 3/1989 | Story et al. | 72/709 X |

FOREIGN PATENT DOCUMENTS 51-100954 9/1976 Japan ..................................... 72/37

OTHER PUBLICATIONS

Grid Circle Analyzer–Computer Aided Measurement of Deformation, Robert A. Ayres et al, Transactions of the Society of Automotive Engineers, 1979–vol. 88 (3), pp. 2630-2634.
MTS Systems Corporation, Minneapolis, Minn. 55424, An Optical Strain Sensor.

*Primary Examiner*—E. Michael Combs
*Attorney, Agent, or Firm*—Craig O. Malin; John C. McFarren

[57] ABSTRACT

A monitor is provided for measuring and controlling the strain rate of a blank during forming. A light source directs light against the blank and a video camera is positioned and focused to view the light reflected from the blank while it is being formed. A video monitor and an image processor receive the signal from the camera. This signal is used to determine the strain rate based upon the dimensional change in reference marks on the blank. The image processor provides an output signal which can be used to control the strain rate in accordance with a predetermined strain rate profile for the particular part being formed.

12 Claims, 2 Drawing Sheets

OPTICAL MONITOR FOR SUPERPLASTIC FORMING

BACKGROUND OF THE INVENTION

This invention relates to the field of material forming, and particularly to superplastic forming of materials.

Under certain conditions, some materials can be plastically deformed without rupture well beyond their normal limits, a property called superplasticity. The usual process involves placing a sheet of material in a die, heating the material to a temperature at which it exhibits superplasticity, and then using a gas to apply pressure to one side of the sheet. Sufficient pressure is applied to strain the material at a strain rate which is within the superplastic range of the material being formed at the selected temperature. This gas pressure creates a tensile stress in the plane of the sheet which causes it to form into the die cavity.

The elongation and thinning characteristics of the material being formed are related to the rate of straining of the material. To shorten forming time and to prevent rupture of the material, it is necessary to use an optimum forming rate throughout the forming operation. As explained in U.S. Pat. No. 4,181,000, this requires continuous adjustment of the forming pressure to account for changes in the blank as it is blown into and against the forming die.

Current superplastic forming technology relies on precalculated pressurization cycles. This approach is inadequate because: (1) the variation in flow properties of the incoming materials can cause significant inaccuracies and irreproducibility in part fabrication, and (2) development of analytical pressure vs time profiles is both costly and requires relatively sophisticated characterization of the materials' superplastic forming properties. To overcome these problems a monitoring device is needed to continuously measure the actual forming strain rate. The monitored strain rate can then be fed back to automatically control the forming operation. However, conventional devices are not applicable because of the high temperature and inaccessibility of the blank being formed. Also, the superplastic blank is soft at the forming temperature and is easily marred by physical contact with the sensor of a monitoring device.

SUMMARY OF THE INVENTION

It is an object of the invention to provide a non-contact device to monitor continuously the strain rate in a blank during superplastic forming.

It is an object of the invention to provide a strain rate monitor which can control superplastic forming to provide the optimum strain rate for forming high quality parts in the shortest time.

According to the invention, a light source is positioned to direct light against the blank while it is being superplastically formed. A video camera is positioned and focused so that it can view reflected light from reference marks on the blank. As the blank stretches to fill the die and form a part, these reference marks and the distance between them grow. A video monitor receives the signal from the video camera and displays the expanding reference marks as the blank is formed. The rate (distance per unit time) at which these reference marks grow is the strain rate of the material.

An image processor receives the output of the video camera in addition to, or in place of, the video monitor. The image processor is programmed to determine the strain rate based upon the change in the reference marks as indicated by the video camera, and to provide a continuous readout of the forming strain rate.

Using this readout, forming pressures are regulated to maintain predetermined optimum forming rates for the particular material and part being formed. A predetermined strain rate profile is entered into the memory of the image processor and is used to provide an output signal from the processor to control the forming pressure and to obtain a strain rate in the material in accordance with the predetermined strain rate profile.

These and other objects and features of the invention will be apparent from the following detailed description taken with reference to the accompanying drawings.

DESCRIPTION OF THE INVENTION

Figure 1:
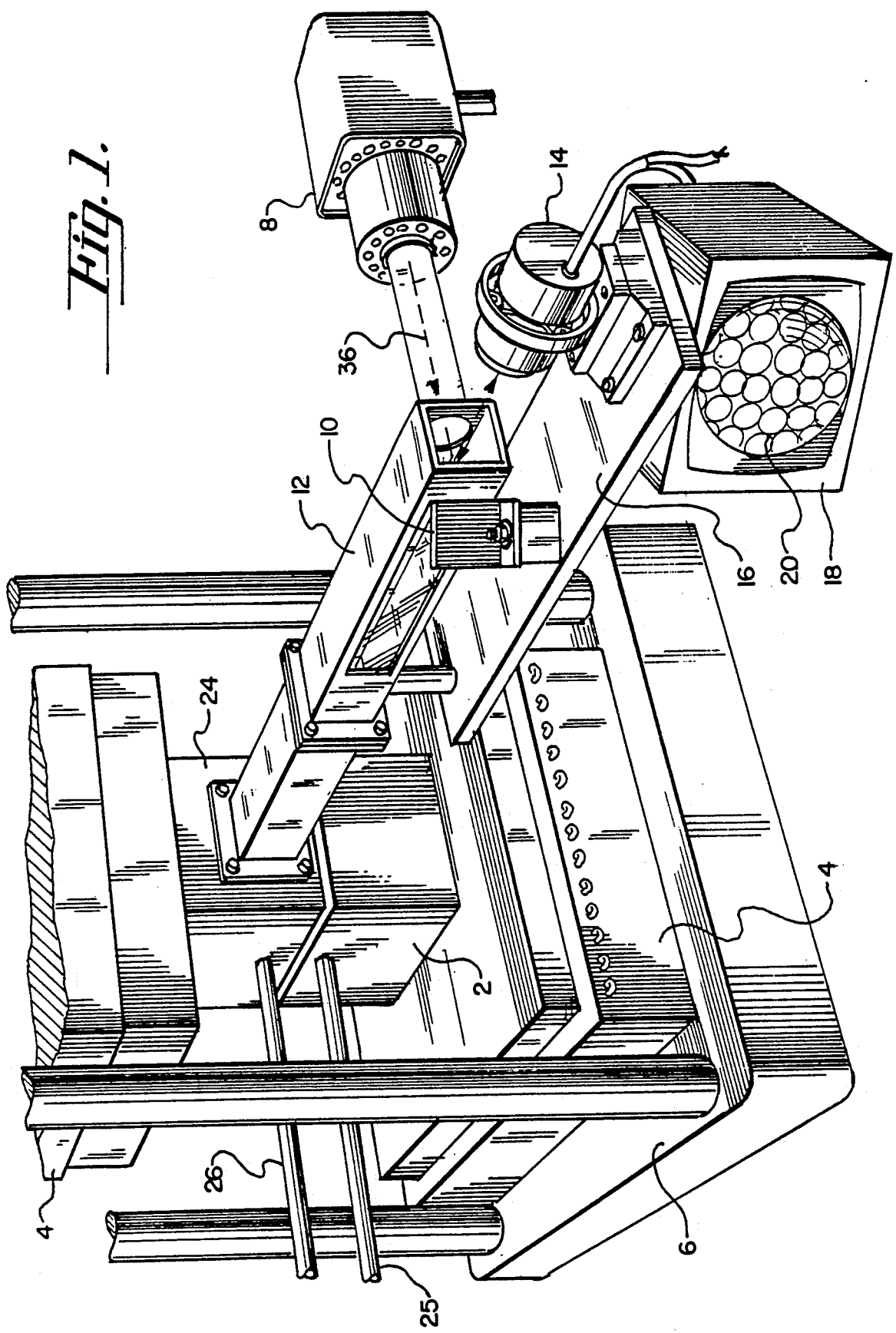
FIG. 1 is a perspective view of the optical monitor of the present invention coupled to a die that is positioned between the heated platens of a press.

FIG. 1 shows the optical monitor being used to visually monitor the strain rate of a blank which is being formed in a die 2 that is heated and held together between the heated platens 4 of a hydraulic press 6. Die 2 has a quartz window through which light can pass in order to view the surface of the blank as it is being formed.

Light source 8 provides a high intensity, uniform distribution of light to illuminate the blank. The light is reflected by an adjustable mirror 10 into and down positioning channel 12, and then into die 2 through the quartz window. This light is reflected off the surface of the forming blank and back through channel 12 into video camera 14. Camera 14 is a high resolution, solid state microvideo camera with optics capable of a long focal length (about 2 ft.) and a large depth of focus (about 4 in.). The camera is mounted on a plate 16 which together with channel 12 provides a support to hold the camera and to position it at the proper location to focus on light reflected from the blank being formed. Channel 12 also serves to locate camera 14 away from heated platens 4 and provide insulation from the heat coming from the platens and from the die.

In this example, the signal from camera 14 is fed to video monitor 18 which displays the surface of the blank with reference marks 20. The illustrated reference marks 20 are a grid pattern of abutting circles which are electro-etched on the blank surface. The optical system used in this example magnifies the grid 4 times relative to the grid on the blank. The diameters of these circles increase as the blank is strained, and the rate at which these diameters grow is the strain rate of the material. For some applications, simple visual monitoring and manual control of the strain rate may be sufficient. However, the operation can be automated using available technology as discussed with regard to FIG. 2.

Figure 2:
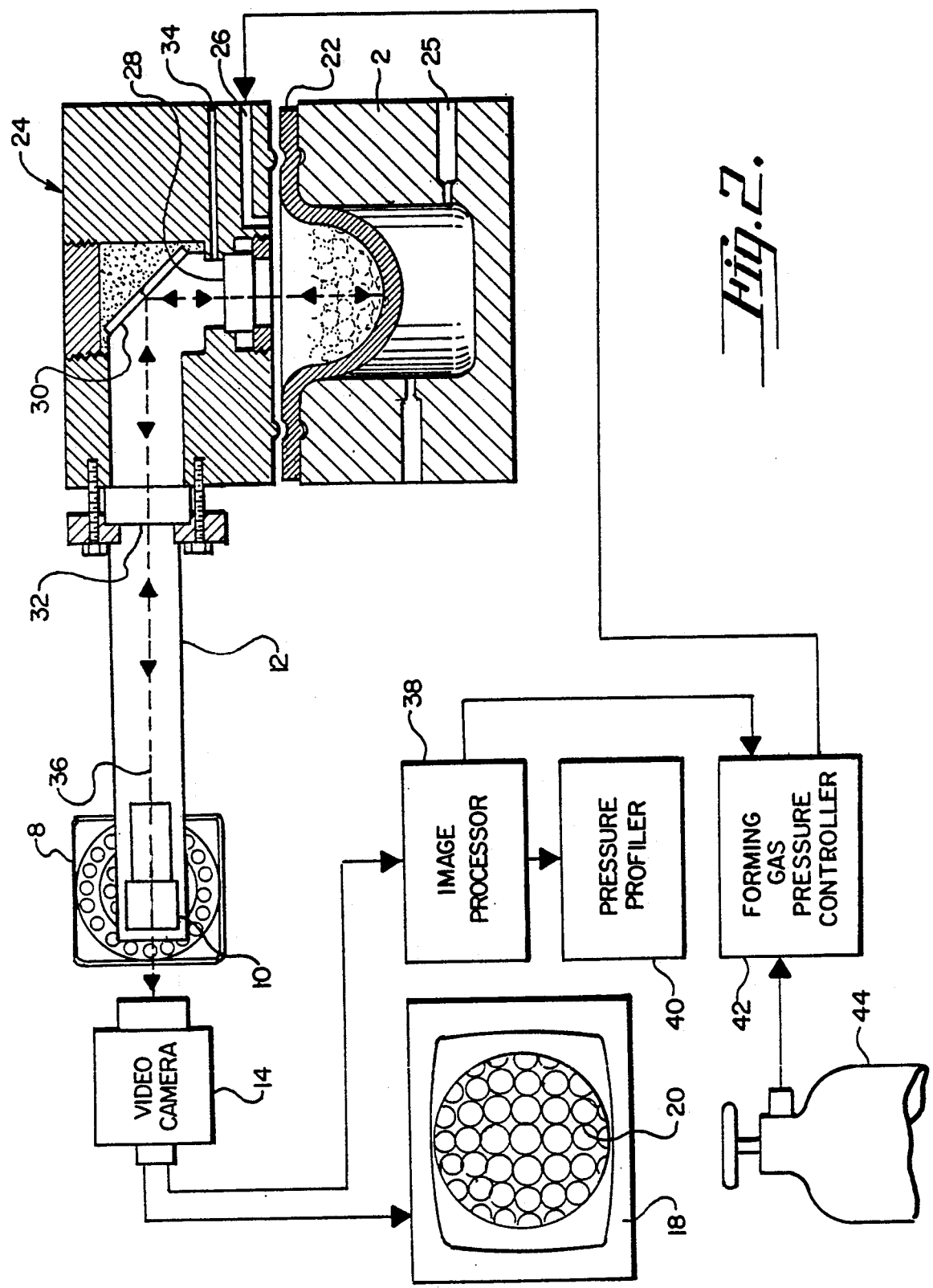
FIG. 2 shows the die in cross section and a schematic of the optical monitor.

A cross section of die 2 is shown in FIG. 2. Blank 22 is formed into the forming chamber of die 2 by means of a gas pressure differential between the surfaces of the blank. In this example, a lid 24 is provided with an inlet 26 to provide pressurized gas on the top side of blank 22. Die 2 is provided with an outlet 25 to vent the die as the blank forms into it. In order to view the surface of blank 22, a high temperature quartz window 28 is provided in lid 24. Because heated platens 4 are used to heat and to hold lid 24 against die 2, a mirror 30 and a second window 32 are provided in the lid so that blank 22 can be viewed from the side. To withstand the forming temperature, mirror 30 is quartz with a reflective chromium surface. A protective atmosphere of argon is provided through inlet 34. Seals are also provided so that a high pressure forming gas can be maintained on the top side of blank 22.

Video camera 14 is held in alignment and spaced from the lid of die 2 by positioning channel 12. As shown if FIG. 1, channel 12 and camera 14 can be supported and held in alignment by plate 16. Light from source 8 is reflected down channel 12 and into the die as shown by dashed line 36.

The signal from the video camera is a picture of the grids on the blank, and this signal is fed into video monitor 18 as described for FIG. 1. Additionally, the video signal is fed to an image processor 38. As the part is formed, the grids expand, and this information is digitized and fed into a computer in the image processor. Using periodic sampling, approximately every 1 to 2 minutes, the strain rate can be determined from the incremental change in grid dimensions. The image processor is programmed with a pressure profiler 40 to indicate the proper strain rate for the particular stage of the forming operation. This predetermined strain rate profile is combined with the actual strain rate for a particular time as determined by the image processor, and this information is used to run a forming gas pressure controller 42. This controller provides the proper gas pressure from gas source 44 to inlet 26. A controller such as described in U.S. Pat. No. 4,181,000 can be used for this purpose.

The preferred embodiments of this invention have been illustrated by the examples described above. Modifications and additional embodiments, however, will undoubtedly be apparent to those skilled in the art. For example, the blank may be viewed directly through the top of the lid, or even from the bottom of the die if the window does not interfere with the shape of the final part. For applications requiring low pressures, a sealed lid may not be required if a vacuum in the forming chamber can provide a sufficient pressure differential to form the part. Furthermore, equivalent elements may be substituted for those illustrated and described herein, and certain features of the invention may be utilized independently of other features. Consequently, the exemplary embodiments should be considered illustrative, rather than inclusive, while the appended claims are more indicative of the full scope of the invention.

What is claimed is:

1. A device for optically monitoring the strain rate of a blank during superplastic forming of the blank against a die, comprising:
   a light source positioned to direct light against the blank while it is being formed against said die;
   a video camera positioned and focused to view light reflected from reference marks on the blank being formed and to provide a video signal of the reflected light;
   a video monitor for receiving the video signal and for displaying the reference marks; and
   means for measuring the strain rate occurring in the blank as it is being superplastically formed as a function of a detected change in dimensions of the reference marks during said superplastic forming of the blank.

2. The device as claimed in claim 1 including a support coupled to the video camera and to the die to hold the video camera in focus with the light reflected from the blank being formed.

3. The device as claimed in claim 2 including a lid for closing one end of the die, the lid being coupled to the support and having a window for viewing light reflected from the blank.

4. The device as claimed in claim 3 wherein the lid has a mirror positioned so that the reflected light can be viewed at right angles to the direction of the forming of the blank.

5. The device as claimed in claim 1, wherein the means for measuring the strain rate comprises an image processor for receiving the video signal and for providing an output signal for controlling the measured strain rate to correspond to a predetermined strain rate.

6. The device as claimed in claim 5 including a forming gas pressure controller which receives the output signal from the image processor and provides gas to the die at a pressure in accordance with the measured strain rate and the predetermined strain rate.

7. The device as claimed in claim 1 wherein the light provided by the light source comprises a high intensity, uniformly distributed light.

8. The device as claimed in claim 1 wherein the video camera comprises a high resolution microvideo camera with optics capable of a long focal length and a large depth of focus.

9. A device for optically monitoring and controlling the strain rate of a blank during superplastic forming of the blank against a die, comprising:
   a light source positioned to direct light against the blank while it is being formed against said die;
   a video camera positioned and focused to view light reflected from reference marks on the blank being formed and to provide a video signal of the reflected light;
   an image processor for receiving the video signal, the image processor having means for determining the strain rate occurring in the blank as it is being superplastically formed as a function of a detected change in dimensions of the reference marks during said superplastic forming of said blank, and having means for providing an output signal for controlling the strain rate based upon a comparison of said determined and predetermined strain rates; and
   a forming gas pressure controller which receives the output signal from the image processor and provides high pressure forming gas to the die in accordance with the output signal so that the determined strain rate corresponds to the predetermined strain rate.

10. Apparatus for monitoring and controlling strain rate of a blank of material during superplastic forming of the blank against a die using gas pressure, comprising:
   a light source positioned to direct light onto the blank while it is being formed against said die;
   video means positioned for receiving light reflected from reference marks on the blank and generating a video signal;
   means for receiving the video signal and measuring the strain rate occurring in the blank as it is being superplastically formed as a function of a detected change in dimensions of the reference marks during said superplastic forming of the blank;

means for comparing the measured strain rate with a predetermined strain rate and generating an output signal; and means for receiving the output signal and controlling the forming gas pressure so that the measured strain rate corresponds to the predetermined strain rate.

11. The apparatus of claim 10, wherein the video signal receiving means comprises an image processor for measuring the strain rate and generating the output signal based on comparison of the measured strain rate with the predetermined strain rate.

12. The apparatus of claim 11, wherein the output signal receiving means comprises a forming gas pressure controller for adjusting the forming gas pressure to control the measured strain rate of the blank during forming.

* * * * *